(12) United States Patent
Chono et al.

(10) Patent No.: US 11,983,961 B2
(45) Date of Patent: May 14, 2024

(54) IMAGE PROCESSING APPARATUS, METHOD, SYSTEM, AND COMPUTER READABLE MEDIUM

(71) Applicant: NEC Corporation, Tokyo (JP)

(72) Inventors: Keiichi Chono, Tokyo (JP); Yuka Ogino, Tokyo (JP); Masato Tsukada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 248 days.

(21) Appl. No.: 17/431,550

(22) PCT Filed: Feb. 12, 2020

(86) PCT No.: PCT/JP2020/005220
§ 371 (c)(1),
(2) Date: Aug. 17, 2021

(87) PCT Pub. No.: WO2020/170894
PCT Pub. Date: Aug. 27, 2020

(65) Prior Publication Data
US 2022/0139114 A1 May 5, 2022

(30) Foreign Application Priority Data
Feb. 18, 2019 (JP) .................... 2019-026941

(51) Int. Cl.
*G06V 40/18* (2022.01)
*G06T 7/246* (2017.01)
(Continued)

(52) U.S. Cl.
CPC ............ *G06V 40/197* (2022.01); *G06T 7/246* (2017.01); *G06V 10/141* (2022.01); *G06V 10/25* (2022.01); *G06V 40/19* (2022.01)

(58) Field of Classification Search
CPC .. G06V 40/165; G06V 40/197; G06V 10/141; G06V 10/25; G06V 40/19; G06T 7/246
See application file for complete search history.

(56) References Cited

U.S. PATENT DOCUMENTS

2008/0316327 A1 12/2008 Steinberg et al.
2010/0118163 A1 5/2010 Matsugu et al.
(Continued)

FOREIGN PATENT DOCUMENTS

JP 2003-050995 A 2/2003
JP 2006-212185 A 8/2006
(Continued)

OTHER PUBLICATIONS

Extended European Search Report for EP Application No. 20758798.1 dated Mar. 11. 2022.
(Continued)

*Primary Examiner* — Margaret G Mastrodonato

(57) ABSTRACT

Iris image pick-up devices perform image pick-up of an iris of a moving subject. A guiding device guides the subject. A controller predicts a period in which the subject will blink next. Further, the controller predicts a period in which the subject will pass through the focusing point of the iris image pick-up devices. The controller controls the guiding device such that the subject does not blink at the focusing point in the case where the period in which the subject will blink next overlaps with the period in which the subject will pass through the focusing point.

15 Claims, 5 Drawing Sheets

(51) Int. Cl.
    *G06V 10/141* (2022.01)
    *G06V 10/25* (2022.01)
    *G06V 40/19* (2022.01)

(56) References Cited

U.S. PATENT DOCUMENTS

| | | | |
|---|---|---|---|
| 2010/0290668 A1 | 11/2010 | Friedman et al. | |
| 2013/0162799 A1* | 6/2013 | Hanna | A61B 5/117 348/78 |
| 2014/0240671 A1* | 8/2014 | Korb | A61B 3/101 351/246 |
| 2015/0256741 A1 | 9/2015 | Towal et al. | |
| 2017/0329138 A1* | 11/2017 | Haddick | G06V 40/197 |

FOREIGN PATENT DOCUMENTS

| | | |
|---|---|---|
| JP | 2007-159610 A | 6/2007 |
| JP | 2017-517165 A | 6/2017 |
| WO | 2009/016846 A1 | 2/2009 |
| WO | 2018/115543 A1 | 6/2018 |

OTHER PUBLICATIONS

JP Office Communication for JP Application No. 2021-501882, dated Oct. 25, 2022 with English Translation.
International Search Report for PCT Application No. PCT/JP2020/005220, dated Apr. 28, 2020.
Masahiko Hosoya, "Identification System by Iris Recognition", Transactions of the Japanese Society for Medical and Biological Engineering 44(1), pp. 33-39. 2006.
John Daugman, "How Iris Recognition Works", pp. 1-10, [Online] <URL: https://www.cl.cam.ac.uk/~jgd1000/irisrecog.pdf>.
IN Office Communication for IN Application No. 292147041267, mailed on Feb. 27, 2024.

* cited by examiner

IMAGE PROCESSING APPARATUS, METHOD, SYSTEM, AND COMPUTER READABLE MEDIUM

This application is a National Stage Entry of PCT/JP2020/005220 filed on Feb. 12, 2020, which claims priority from Japanese Patent Application 2019-026941 filed on Feb. 18, 2019, the contents of all of which are incorporated herein by reference, in their entirety.

TECHNICAL FIELD

The present disclosure relates to an image processing apparatus, a method, a system, and a computer readable medium, and in particular to an image processing apparatus, a method, a system, and a computer readable media that can be used for authentication using an iris(es).

BACKGROUND ART

Biometric authentication using an iris(es) has been known. In such biometric authentication, iris(es) of a subject is photographed by using an image pick-up apparatus, and feature values are extracted from the pattern of the photographed iris. In order to authenticate a subject, extracted feature values are compared with those registered in advance in a database, and a pass/fail is determined based on a score of matching therebetween. Further, in order to register a subject to be authenticated, extracted feature values are added in the database.

As described in Non-patent Literature 1, an iris, which is a donut-shaped tissue surrounding a pupil, has a very complex pattern, and is unique to each person. Further, in the photographing of an iris, near-infrared light is applied to eyes of a subject.

As described in Non-patent Literature 2, in the photographing of an iris(es), an image of the iris is taken with a resolution in which the radius of the iris is expressed by 100 to 140 pixels. Further, the wavelength of the near-infrared light applied to the eyes of the subject is in a range between 700 nm and 900 nm.

CITATION LIST

Non Patent Literature

Non-patent Literature 1: Hosoya, "Identification System by Iris Recognition", Japanese Society for Medical and Biological Engineering 44(1), pages 33-39, 2006

Non-patent Literature 2: Daugman, "How Iris Recognition Works," https://www.cl.cam.ac.uk/~jgd1000/irisrecog.pdf

SUMMARY OF INVENTION

Technical Problem

The diameter of an iris is about 1 cm. Therefore, when the radius of an iris is expressed by 100 pixels, the granularity becomes 50 μm. Since the pattern of an iris is microscopic as described above, it is difficult to photograph an iris pattern at a level of quality sufficient for authentication and verification under conditions that distance between the subject and the image pick-up means is large, a field of view to be photographed is wide, and the subject moves.

In light of the above circumstances, an object of the present disclosure is to provide an image processing apparatus, method, system, and computer-readable medium capable of photographing an iris pattern at a level of quality sufficient for authentication and verification.

Solution to Problem

In order to achieve the above-described object, in a first aspect, the present disclosure provides an image processing system including:
 a plurality of iris image pick-up means disposed at mutually different positions in the same field of view;
 overall image pick-up means for performing image pick-up over a wider field of view than the field of view of the iris image pick-up means;
 guiding means for guiding a subject;
 illumination means for illuminating the subject with light; and
 control means for controlling, using an image from the overall image pick-up means, at least one of reading out an image from the plurality of iris image pick-up means, presenting at least one of an image and a sound through the guiding means, or providing illumination with light from the illumination means, wherein
 the control means further predicts a period in which the subject will blink next and a period in which the subject will pass through a focusing point of the iris image pick-up means, and in a case where the period in which the subject will blink next overlaps with the period in which the subject will pass through the focusing point, the control means controls at least one of the guiding means or the iris image pick-up means such that the focusing point and a position where the subject will blink next are different.

In a second aspect, the present disclosure provides an image processing apparatus including:
 control means for predicting a period in which a moving subject will blink next and a period in which the subject will pass through a focusing point of iris image pick-up means for performing image pick-up of an iris of the subject, and in a case where the period in which the subject will blink next overlaps with the period in which the subject will pass through the focusing point, controlling guiding means for guiding the subject such that the subject does not blink at the focusing point.

In a third aspect, the present disclosure provides an image processing apparatus including:
 control means for predicting a period in which a moving subject will blink next and a period in which the subject will pass through a focusing point of iris image pick-up means for performing image pick-up of an iris of the subject, and in a case where the period in which the subject will blink next overlaps with the period in which the subject will pass through the focusing point, controlling the iris image pick-up means such that the focusing point is a position other than the position of the subject in the period in which the subject will blink next.

In a fourth aspect, the present disclosure provides an image processing method including:
 performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

In a fifth aspect, the present disclosure provides an image processing method including:
   predicting a period in which a moving subject will blink next;
   predicting a period in which the subject will pass through a focusing point of iris image pick-up means for performing image pick-up of an iris of the subject;
   determining whether or not the period in which the subject will blink next overlaps with the period in which the subject will pass through the focusing point; and
   performing, in a case of determining that the periods overlap, at least one of guiding the subject or controlling the iris image pick-up means such that the focusing point and a position where the subject will blink next are different.

In a sixth aspect, the present disclosure provides a non-transitory computer readable medium storing a program causing a computer to execute a process including:
   performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

In a seventh aspect, the present disclosure provides a non-transitory computer readable medium storing a program causing a computer to execute a process including:
   predicting a period in which a moving subject will blink next;
   predicting a period in which the subject will pass through a focusing point of iris image pick-up means for performing image pick-up of an iris of the subject;
   determining whether or not the period in which the subject will blink next overlaps with the period in which the subject will pass through the focusing point; and
   performing, in a case of determining that the periods overlap, at least one of guiding the subject or controlling the iris image pick-up means such that the focusing point and a position where the subject will blink next are different.

Advantageous Effects of Invention

An image processing apparatus, a method, a system, and a computer readable medium according to the present disclosure is capable of photographing an iris pattern at a level of quality sufficient for authentication and verification.

DESCRIPTION OF EMBODIMENTS

Prior to giving the description of an example embodiment according to the present disclosure, a problem thereof is quantitively described. As an example, the below-shown conditions, which are assumed as operational conditions for Automated Border Control systems (ABC systems) and the like, will be described hereinafter. It is assumed that a distance between a subject and image pick-up means (the distance between a subject and a gate) is 2 m, and a horizontal field of view, i.e., a range in the horizontal direction in which both eyes of one subject can be covered, is 0.2 m. Further, a vertical field of view, i.e., a range in the vertical direction in which the eyes of a wide range of subjects from a tall subject, typically a male person, to a short subject, typically a female person, can be covered, is 0.4 m. Further, it is assumed that the walking speed (the moving speed) of the subject relative to the gate is equal to the average of slow walking speeds of adult people, e.g., is 1 m/s.

Under the above operating conditions, assuming that an image sensor with a pixel pitch of 5 μm and a lens with an aperture stop of F2 and a focal length of 200 mm are used, both a high resolution of 32 M pixels and a high frame rate of 100 frames per second (fps) are demanded from the image pick-up means, as described later.

With regard to resolution, to secure a 0.2 m horizontal field of view at a position 2 m away from the image pick-up apparatus, the image pick-up apparatus needs 4000 pixels (0.2 [m]÷50 [μm]=4000) in the horizontal direction. Further, to secure a 0.4 m vertical field of view at a position 2 m away from the image pick-up apparatus, the image pick-up apparatus needs 8000 pixels (0.4 [m]÷50 [μm]=8000) in the vertical direction. As a result, a resolution of 32 M pixels is demanded from the image pick-up apparatus.

On the other hand, in the case where the above lens is used, if the allowable circle of confusion diameter is 0.03 mm, the depth of field that can be secured 2 m away is approximately 1 cm. In the case where the subject has a walking speed of 1 m/s, the time it takes for the subject to pass through the 1 cm subject depth is 1 [cm]÷100 [cm/s] =0.01 s. In this case, to capture the 0.01 s instant when the iris of the walking subject is in focus, a performance of 100 fps (1 [s]÷100 [fps]=0.01 s time resolution) is demanded from the image pick-up apparatus.

Image pick-up equipment capable of satisfying a high resolution of 32 M pixels and a high frame rate of 100 fps with a single device does not exist as a popular product. Consequently, photographing an iris pattern at a level of quality sufficient for authentication and verification under the operating conditions described above is difficult. This concludes the quantitative description of the problem.

Figure 1:
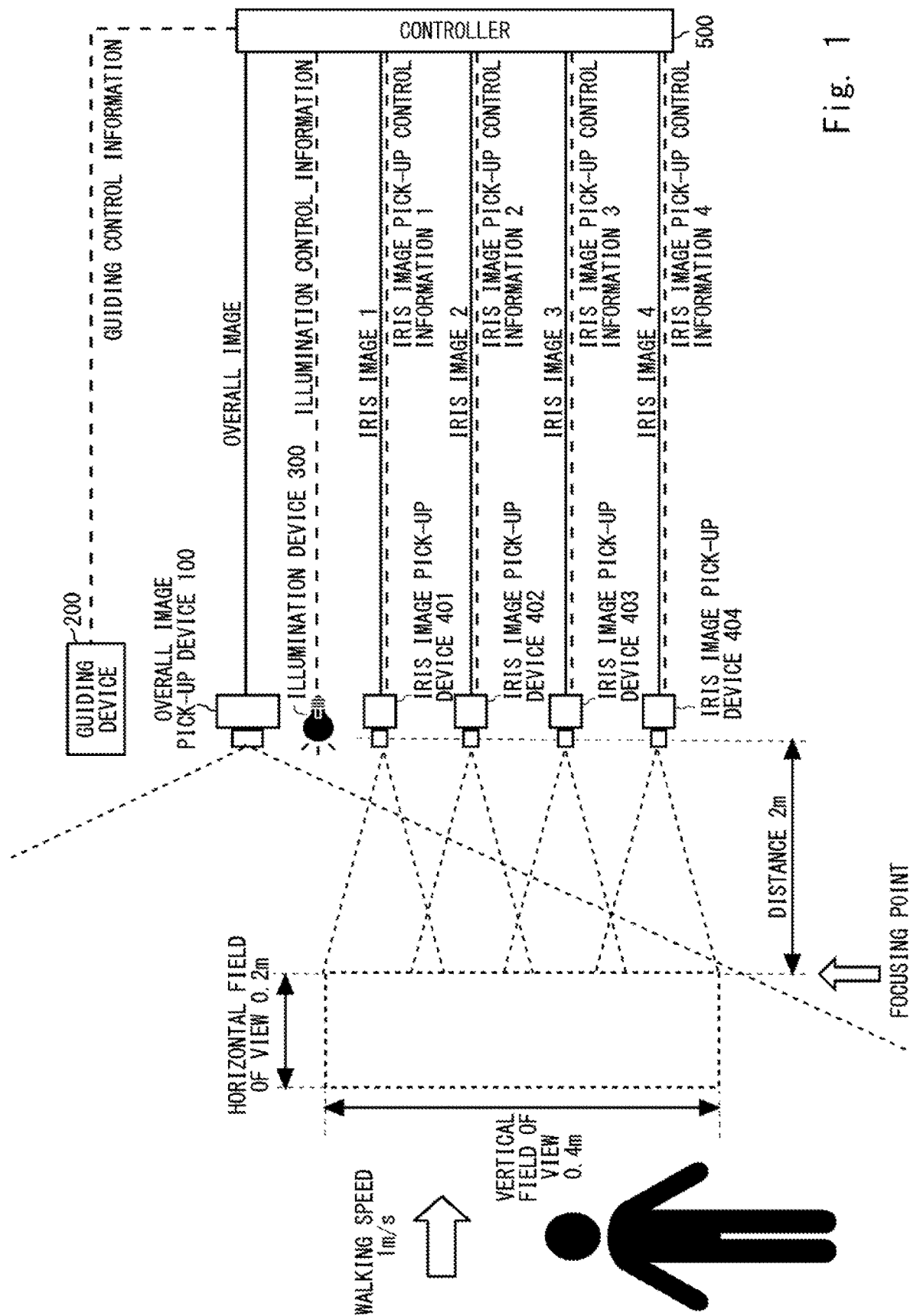
FIG. 1 is a block diagram showing an image processing system according to a first example embodiment of the present disclosure.

Example embodiments according to the present disclosure will be described hereinafter with reference to the drawings. FIG. 1 shows an image processing system according to a first example embodiment of the present disclosure. The image processing system includes an overall imaging device 100, a guiding device 200, an illumination device 300, iris image pick-up devices 401 to 404, and a controller 500. Note that although the number of iris image pick-up devices is four in FIG. 1, the number of iris image pick-up devices is not limited to any particular number. The number of iris image pick-up devices can be set as appropriate according to the field of view to be covered and the resolutions of available iris image pick-up devices.

The overall imaging device (overall image pick-up means) 100 photographs a subject with a wide field of view that is wide enough to cover a whole range of subjects from a tall subject to a short subject. The overall imaging device 100 may have a resolution in which a subject can be authenticated by his/her face.

The controller (control means) 500 monitors an overall image supplied from the overall imaging device 100, and controls the guiding device (guiding means) 200, the illumination device (illumination means) 300, and the plurality of iris image pick-up devices (iris image pick-up means) 401 to 404. The functions of the controller 500 can be implemented by hardware or by a computer program(s). The controller 500 determines a start of biometric authentication for the subject based on his/her overall image supplied from the overall imaging device 100, or based on an external input.

The control performed by the controller 500 includes guiding control, illumination control, and iris image pick-up control. In the guiding control, the controller 500 supplies guiding control information for guiding the subject to the guiding device 200. The guiding device 200 guides the subject based on the guiding control information. The guiding device 200 includes, for example, a display and/or a speaker(s). For example, the guiding device 200 presents an image(s) and a sound(s) for indicating the start of biometric authentication through the display and/or the speaker, respectively. Further, the guiding device 200 presents images and sounds for inducing the subject to turn his/her eyes to the iris image pick-up devices through the display and/or the speaker, respectively.

In the illumination control, the controller 500 supplies, to the illumination device 300, illumination control information for applying illumination light to the subject. The illumination device 300 applies light (e.g., near-infrared light) to the subject based on the illumination control information. The illumination device 300 includes LEDs (Light Emitting Diodes) as a light source, and a synchronization signal generator. The amount of light applied from the illumination device 300 to the subject is determined by the value of the current supplied to the LEDs, the lighting time of the LEDs, and the lighting cycle thereof, and the illumination control information includes the numerical values thereof. When the LEDs are not continuously kept in the on-state, the lighting cycle of the LEDs is synchronized with the frame rates of the plurality of iris image pick-up devices 401 to 404.

In the iris image pick-up control, the controller 500 determines, based on the overall image supplied from the overall imaging device 100, one of the plurality of iris image pick-up devices 401 to 404 that can suitably photograph an area of the subject including his/her eyes. Further, the controller 500 determines the vertical position of a region of interest that is read out at a high speed in the determined iris image pick-up device.

Figure 2:
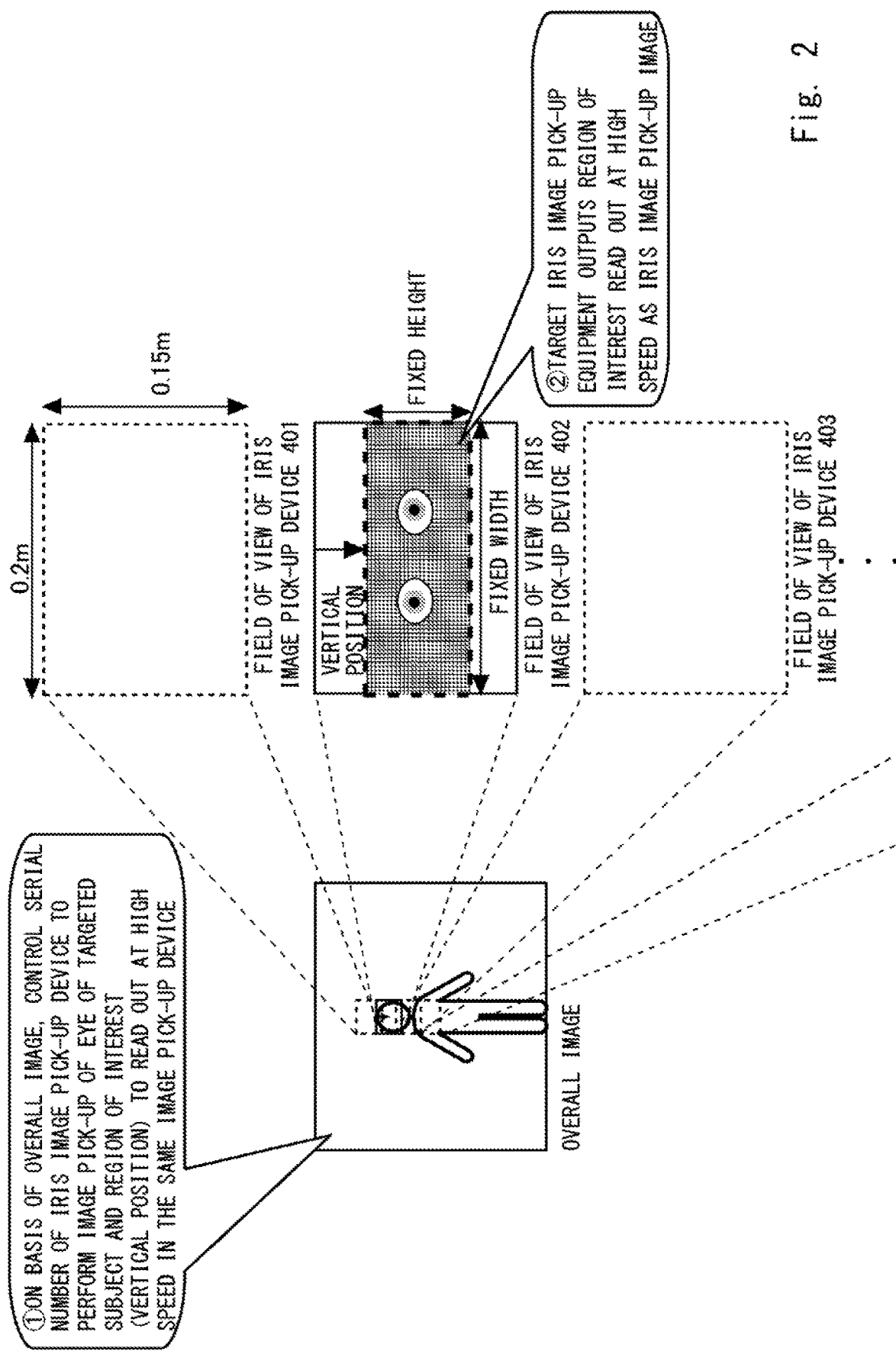
FIG. 2 shows a state of iris image pick-up control.

FIG. 2 shows a state of the iris image pick-up control. Details of the iris image pick-up control will be described with reference to FIG. 2. In this example, it is assumed that a general-purpose camera having 12 M pixels (4,000 horizontal pixels and 3,000 vertical pixels) and a frame rate of 60 fps is used for each of the iris image pick-up devices 401 to 404. Such cameras have been becoming widespread as industrial cameras. In the case where the photographing is performed with a granularity of 50 μm, with which a subject can be authenticated by his/her iris, the horizontal and vertical fields of view of each of the iris image pick-up devices are 0.2 m (4,000×50 [μm]=0.2 [m]) and 0.15 m (3,000×50 [μm]=0.15 [m]), respectively.

The plurality of iris image pick-up devices 401 to 404 are arranged so that they are stacked on top of each other in the vertical direction. Note that the plurality of iris image pick-up devices 401 to 404 are arranged so that the image areas of iris image pick-up devices adjacent to each other partially overlap each other. For example, the iris image pick-up devices 401 to 404 are arranged so that the image areas of iris image pick-up devices adjacent to each other overlap each other by 2.5 cm. In such a case, at the focusing point 2 m away from the four iris image pick-up devices, they can secure a field of view of 0.2 m in the horizontal direction and 0.45 m ((0.15−0.025)+(0.15−0.025−0.025)+(0.15−0.025−0.025)+(0.15−0.025)  m) in the vertical direction. That is, it is possible to secure the required field of view of 0.2 m in the horizontal direction and 0.4 m in the vertical direction. Note that it can be understood, by the drawings and the above description, that the iris image pick-up devices have the same fields of view as each other and are placed in positions different from each other.

In the case where the frame rate of each of the iris image pick-up devices is 60 fps, they cannot meet the required frame rate of 100 fps when they are used as they are. Note that an industrial camera or the like has a region-of-interest mode. In the region-of-interest mode, only a partial area that is defined as a region of interest is read out instead of reading out the entire area of the screen. It is possible to increase the frame rate by using such a region-of-interest mode.

The controller 500 sets a region of interest in any given iris image pick-up device and reads out the image in the region of interest from that iris image pick-up device. In the example shown in FIG. 2, a partial area of 4,000 pixels in the horizontal direction and 1,500 pixels in the vertical direction, which corresponds to a half of the entire area of the screen, is defined as the region of interest. In this case, since the number of pixels in each frame is a half of the number of pixels in the entire area, it is possible to increase the frame rate to 120 fps, which is twice the frame rate of 60 fps in the case where the entire area of the screen is read out. However, the horizontal and vertical fields of view of the partial area become 0.2 m and 0.75 m, respectively. Note that both eyes of a human being are aligned in the horizontal direction. Therefore, in the region-of-interest, it is preferred to reduce the number of pixels in the vertical direction, instead of reducing that in the horizontal direction, so that both eyes can be photographed.

Under the condition that the area of eyes is not photographed in the above-described range where the image areas of iris image pick-up devices adjacent to each other overlap each other, the iris image pick-up device that photographs the area of eyes is only one of the four iris image pick-up devices 401 to 404. Further, the condition under which the image can be read out at the frame rate of 120 fps is a partial area in that iris image pick-up device. The controller 500 infers one of the iris image pick-up devices 401 to 404 that can suitably photograph the area of eyes, and estimates the vertical position of the region of interest in which the image is read out at a high speed in that iris image pick-up device.

The above-described inference/estimation can be carried out by a method described below. The overall imaging device 100 has a resolution in which a subject can be authenticated by his/her face, and the controller 500 derives the positions of the eyes of the subject in the overall image taken by the overall imaging device 100. The controller 500 derives the iris image pick-up device corresponding to the positions of the eyes of the subject in the overall image and the positions of the eyes present in that imaging device by using camera parameters and the positional relation of the overall imaging device 100 and each of the iris image pick-up devices. By using the region-of-interest mode, it is possible, by using a general-purpose camera, to achieve a field of view wider than 0.2 m in the horizontal direction and 0.4 m in the vertical direction, and a temporal resolution higher than 100 fps.

Note that when the vertical position is changed in the above-described region-of-interest mode, a delay occurs before the start of the photographing. Therefore, in the above-described inference/estimation, an image that is obtained by photographing the subject at a position that is more distant than the position 2 meters away, i.e., more distant than the focusing point of the iris image pick-up device, e.g., by photographing the subject at a position 3 meters away may be used. The resolution in which a subject present at a position 3 meters away can be authenticated by his/her face can be achieved by a camera having about 2 M pixels, so that cameras having specifications lower than those of the iris image pick-up cameras can be used for the overall imaging device 100.

The controller 500 supplies iris image pick-up information to each of the iris image pick-up devices 401 to 404 based on the above-described iris image pick-up control. The controller 500 supplies iris image pick-up information including the vertical position of the region of interest to the iris image pick-up device that photographs the area of the eyes of the subject. The controller 500 may supply optional iris image pick-up information to the other iris image pick-up devices. The controller 500 may supply iris image pick-up information including information about the stop of the supply of the iris image to the other iris image pick-up devices, for example, in order to reduce the total amount of the data of the iris image.

Each of the iris image pick-up devices 401 to 404 supplies the iris image to the controller 500 based on the iris image pick-up information supplied from the controller 500. Note that each of the iris image pick-up devices 401 to 404 outputs the image in the region of interest that is set by the controller 500 by using the iris image pick-up information (i.e., the iris image) to the controller 500. Each of the iris image pick-up devices 401 to 404 may lossy-compress the iris image in the region of interest and output the compressed iris image to the controller 500. For example, each of the iris image pick-up devices 401 to 404 compresses the iris image in the region of interest by using quantization (pixel-by-pixel compression), predictive coding and quantization (compression on a basis of a plurality of pairs of pixels), or a combination of transform coding and quantization (compression on a basis of a plurality of pairs of pixels). The controller 500 performs the authentication and the registration described in the background section by using the iris images supplied from the iris image pick-up devices 401 to 404. The controller 500 returns to the next process when there is a next subject or when the authentication or the registration has failed.

Figure 3:
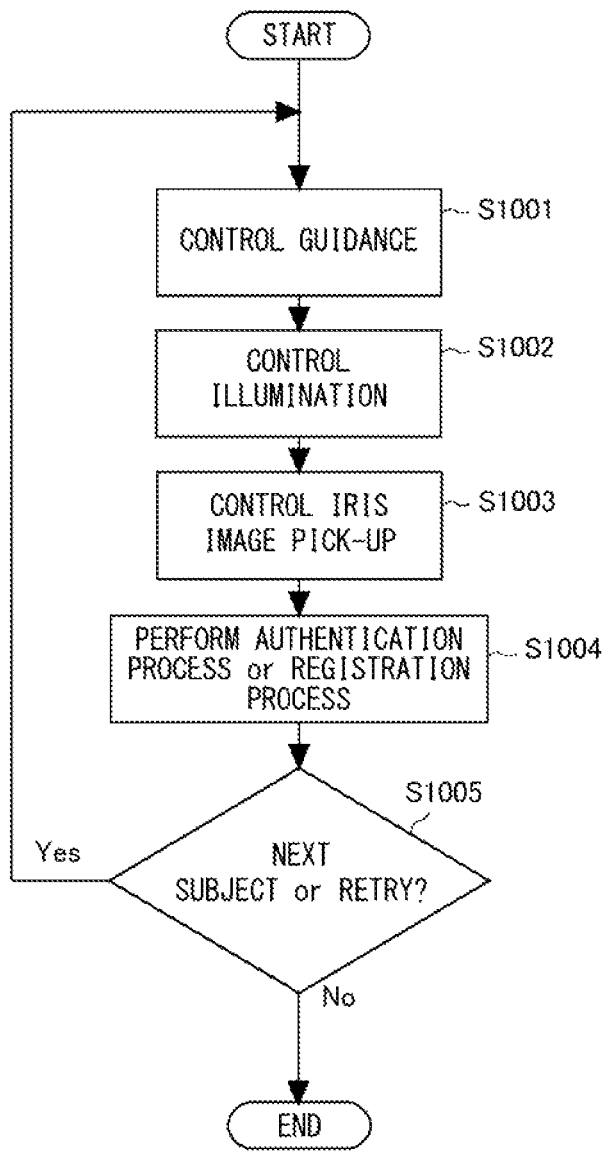
FIG. 3 is a flowchart showing an operational procedure in an image processing system.

Next, an operational procedure will be described. FIG. 3 shows an operational procedure in the image processing system. The controller 500 performs guiding control and thereby guides a subject by using the guiding device 200 (step S1001). The controller 500 performs the illumination control and thereby applies infrared light to the subject by using the illumination device 300 (step S1002). The controller 500 performs the above-described iris image pick-up control and thereby acquires an image(s) of an iris(es) (an iris image(s)) by using the plurality of iris image pick-up devices 401 to 404 (step S1003). The iris image(s) acquired in the step S1003 is used for the authentication or registration of the iris. In the step S1003, the controller 500 does not need to obtain the iris image from each of the iris image pick-up devices 401 to 404 for a given subject as described above. The controller 500 obtains the iris image from the iris image pick-up device that has photographed the area of the eyes of the subject.

The controller 500 performs iris-based authentication by using the iris image acquired in the step S1003, or registers the iris image (step S1004). The controller 500 determines whether or not there is a next subject, or whether or not re-authentication or re-registration should be performed (step S1005). When it is determined that there is a next subject, or re-authentication or re-registration should be performed, the process returns to the step S1001 and the process is performed starting from the guiding control.

Note that when the overall imaging device 100 according to this example embodiment has a resolution in which a subject can be authenticated by his/her face, and holds feature values for authenticating the subject by his/her face in a database but does not hold feature values for authenticating the subject by his/her iris in the database, the apparatus according to the present disclosure can also be used for a use in which the apparatus identifies a subject based on face-based authentication and registers extracted feature values of the iris(es) of the subject in the database. Further, the apparatus according to the present disclosure can also be used for a use in which the apparatus estimates information about the height of a subject based on information about the positions of the eyes obtained by the iris image pick-up control, or information about the positions of the eyes that is obtained when an iris image obtained by the iris image pick-up device is authenticated or registered, and registers the estimated information in the database. Further, the apparatus according to the present disclosure can be used, by using the estimated information about height, to determine or calibrate the vertical position of one of iris image pick-up devices that can suitably photograph the area of eyes and the region of interest in which the image is read out at a high speed in that iris image pick-up device.

In this example embodiment, a high resolution supporting the demanded 0.2 m×0.4 m field of view and a high frame rate performance corresponding to a time resolution of 0.01 s can be achieved with a combination of general-purpose cameras. As a result, it is easy to photograph an iris pattern at a level of quality sufficient for authentication and verification under conditions such as when there is a long distance between the subject and the image pick-up means, a wide field of view to be photographed, and the subject moves.

Next, a second example embodiment of the present disclosure will be described. The configuration of an image processing system according to the example embodiment may be similar to the configuration of the image processing system in the first example embodiment illustrated in FIG. 1. In the present example embodiment, the controller 500 respectively predicts the next blink occurrence period of the subject and the period in which the subject will pass through the focusing point (2 m away) of the iris image pick-up devices. The controller 500 controls the guiding device 200 such that blinking does not occur at the focusing point when these periods overlap. In the present example embodiment, the controller 500 also functions as an image processing apparatus (control apparatus) that performs an image processing method (control method) related to blinking. Otherwise, the configuration may be similar to the first example embodiment.

Since blinking is a physiological phenomenon that is difficult to control even with the subject's own effort, there is a possibility that blinking may occur at the focusing point of the iris image pick-up devices 401 to 404. Humans blink an average of 20 times per minute (interval time 3 s) with each blink lasting 0.2 s (duration 0.2 s), and the time ratio of the eyes being open is 93.3%. Calculated simply, the retry probability for authentication and registration due to blinking is 6.6%, and approximately 7 out of 100 people will have to retry authentication or registration.

The controller 500 can acquire information about whether or not the subject's eyes are closed by analyzing the eye region of the overall image from the overall image pick-up device 100. In addition, the controller 500 can also acquire distance information about the distance to the subject by using an overall image pick-up device 100 that includes a distance measurement function such as time of flight (ToF). The controller 500 can acquire not only position information about the subject but also information about the walking speed of the subject by analyzing the distance information in a time series.

Next, for the description hereinafter, the information about whether or not the subject's eyes are closed, the position information about the subject, the walking speed of the subject, the blink interval time, the blink duration, information about the focusing point, and information about an in-focus range are defined as follows.

Let $b(t)$ be the information about whether or not the subject's eyes are closed at a time t. Here, let $b(t)=1$ denote that the subject's eyes are closed. Also, let $b(t)=0$ denote that the subject's eyes are open. That is, $b(t)=1$ corresponds to blinking, and $b(t)=0$ corresponds to not blinking.

Let $d(t)$ [m] be the position information about the subject, namely the distance from the overall image pick-up device 100 to the subject, at the time t. Let v [m/s] be the average walking speed of the subject. Let $b\_i\_t$ [s] be the blink interval time. Let $b\_p\_t$ [s] be the blink duration. Let df [m] be the information about the focusing point, namely the distance from the iris image pick-up devices 401 to 404 to the focusing point. Let dof [m] be the information about the in-focus range. This completes the definition of each piece of information.

The controller 500 can predict the next blink occurrence period of the subject as follows (hereinafter also referred to as next blink period prediction). The controller 500 searches for the last time tblast at which $b(t)=1$ in a period ($tc-b\_i\_t \leq t \leq tc$) going back $b\_i\_t$ seconds from the current time tc. The controller 500 treats the value obtained by adding $b\_i\_t$ and subtracting $b\_p\_t$ from tblast as the next blink occurrence start time tbnext ($=tblast+b\_i\_t-b\_p\_t$). The controller 500 predicts the time from the next blink occurrence start time tbnext until $tbnext+b\_p\_t$ ($tbnext \leq t \leq tbnext+b\_p\_t$) as the next blink occurrence period.

The controller 500 can predict the period in which the subject will pass through the focusing point as follows (hereinafter also referred to as focusing point pass-through period prediction). The controller 500 calculates a time ta at which the subject at the distance $d(t)$ at the time t will reach the focusing point. The time ta can be calculated by subtracting the distance df from the distance $d(t)$, dividing the result by the walking speed v, and adding the resulting time to the time t. In other words, $ta=t+(d(t)-df)/v$. The controller 500 predicts the period from the time ta until the time obtained by adding the time during which the subject will pass through the in-focus range to the time ta ($ta \leq t \leq ta+(dof \div v)$) as the period in which the subject will pass through the focusing point.

The controller 500 determines whether or not the next blink occurrence period of the subject derived as above overlaps with the period in which the subject will pass through the focusing point. In the case where the next blink occurrence period and the period in which the subject will pass through the focusing point overlap, the controller 500 uses the guiding device 200 to guide the subject such that blinking does not occur at the focusing point (hereinafter also referred to as blink avoidance guiding control).

In the blink avoidance guiding control, the controller 500 controls the guiding device 200 to delay the time at which the subject will reach the focusing point, for example. In this case, the controller 500 causes the guiding device 200 to use the display or speaker to present information such as an image or sound for causing the subject to "slow down" or "stand still". By causing the subject to follow the guidance and lower the walking speed or temporarily stand still, the time at which the subject will reach the focusing point can be delayed, and the probability of successfully avoiding blinking at the focusing point can be increased.

In the blink avoidance guiding control, the controller 500 may also control the guiding device 200 to hasten the time at which the subject will reach the focusing point. In this case, the controller 500 causes the guiding device 200 to use the display or speaker to present information such as an image or sound for causing the subject to "speed up". By causing the subject to follow the guidance and raise the walking speed, the time at which the subject will reach the focusing point can be hastened, and the probability of successfully avoiding blinking at the focusing point can be increased.

In the blink avoidance guiding control, the controller 500 may also control the guiding device 200 to cause the subject to blink. For example, in the case where $b(t)$ cannot be stored for a long time, the controller 500 may cause the display or speaker to present information such as an image or sound for asking the subject to "please blink" in the period until a time obtained by subtracting the blink duration from the time ta. In this case, by causing the subject to blink once before passing through the focusing point, it is possible to keep blinking from occurring in the period in which the subject passes through the focusing point. Furthermore, in the case where the iris image pick-up means includes a function of moving the focusing point, the controller 500 may also move the focusing point such that the subject is in focus outside the next blink occurrence period. The function of moving the focusing point can be achieved by driving a means for controlling the point of focus, such as a liquid lens provided in the iris image pick-up device, for example.

Figure 4:
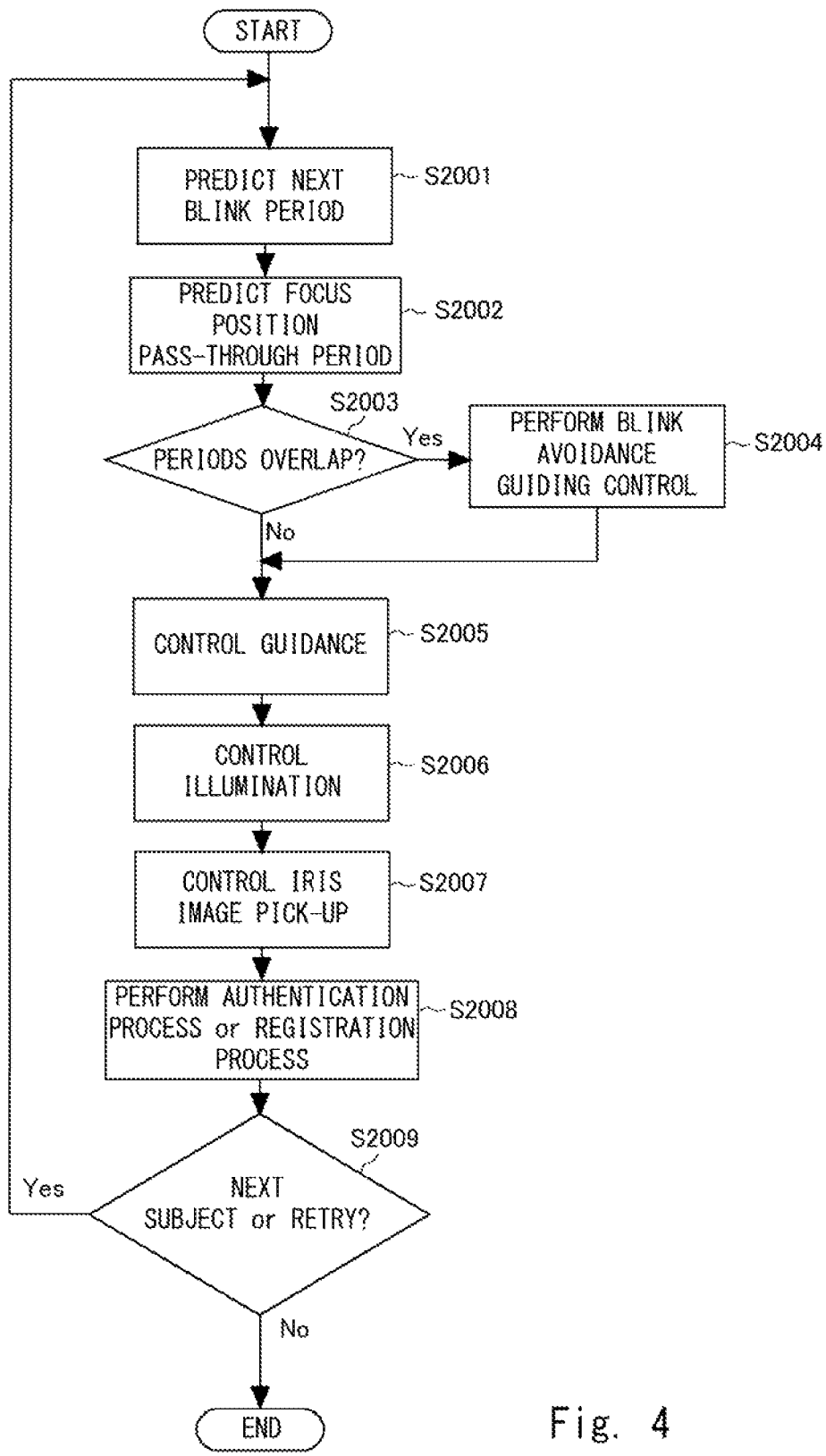
FIG. 4 is a flow chart showing an operational procedure in an image processing system according to a second example embodiment of the present disclosure.

Next, an operational procedure will be described. FIG. 4 illustrates an operational procedure in the image processing system. The controller 500 performs the next blink period prediction described above (step S2001). In additionally, the controller 500, the controller 500 performs the focusing point pass-through period prediction described above (step S2002). The controller 500 determines whether or not the next blink period predicted in step S2001 and the focusing point pass-through period predicted in step S2002 overlap (step S2003). In the case where the controller 500 determines that the periods overlap in step S2003, the controller 500 performs the blink avoidance guiding control described above, and guides the subject using the guiding device 200 (step S2004).

The controller 500 performs the guiding control described in the first example embodiment, and guides the subject using the guiding device 200 (step S2005). The controller 500 performs the illumination control and irradiates the subject with infrared light using the illumination device 300 (step S2006). The controller 500 performs the iris image pick-up control and acquires an image of the iris (iris image) picked up using the plurality of iris image pick-up devices 401 to 404 (step S2007). In step S2007, as described in the first example embodiment, the controller 500 does not need to obtain iris images for a certain subject from all of the iris image pick-up devices 401 to 404. The controller 500 acquires an iris image from each iris image pick-up device performing image pick-up of the eye region of the subject.

The controller 500 performs iris authentication using the iris image(s) acquired in step S2007, or registers the iris image(s) (step S2008). The controller 500 determines whether or not there is a next subject, or whether or not re-authentication or re-registration should be performed (step S2009). In the case of determining that there is a next subject or that re-authentication or re-registration should be performed, the process returns to step S2001, and the process is performed from the next blink period prediction. Steps S2005 to S2009 may be similar to steps S1001 to S1005 in FIG. 3.

In the present example embodiment, the controller 500 predicts the next blink period of the subject. Further, the controller 500 predicts the period in which the subject will pass through the focusing point of the iris image pick-up devices. In the case where the next blink period and the period in which the subject will pass through the focusing point overlap, the controller 500 performs the blink avoidance guiding control, and uses the guiding device 200 to guide the subject. With this arrangement, the probability of successfully avoiding blinking by the subject at the focusing position can be increased, and the retry rate of authentication and registration caused by blinking can be lowered.

Note that although an example in which a partial area of 4,000 pixels in the horizontal direction and 1,500 pixels in the vertical direction is defined as the region of interest in FIG. 2, the present disclosure is not limited to this example. The shape of the region of interest is not limited to the rectangle, and the number of region of interest s is not limited to one. The controller 500 may, for example, derive the positions of the right eye and left eye of the subject from the overall image (the overlooked image) taken by the overall imaging device 100, and set a region of interest corresponding to the position of the right eye and a region of interest corresponding to the position of the left eye in the iris image pick-up device. In such a case, the iris image pick-up device supplies iris images of the right and left eyes to the controller 500. The shape of the region of interest may be rectangular or may be elliptic. The controller 500 may derive the positions of the right and left eyes of the subject based on the iris image taken by the iris image pick-up device instead of based on the overlooked image. For example, the controller 500 may temporarily define the partial area shown in FIG. 2 as the region of interest, and derive the positions of the right and left eyes from the images in the region of interest. In such a case, the controller 500 may set, based on the derived positions of the right and left eyes, each of a partial area corresponding to the position of the right eye and a partial area corresponding to the position of the left eye as a region of interest in the iris image pick-up device.

Figure 5:
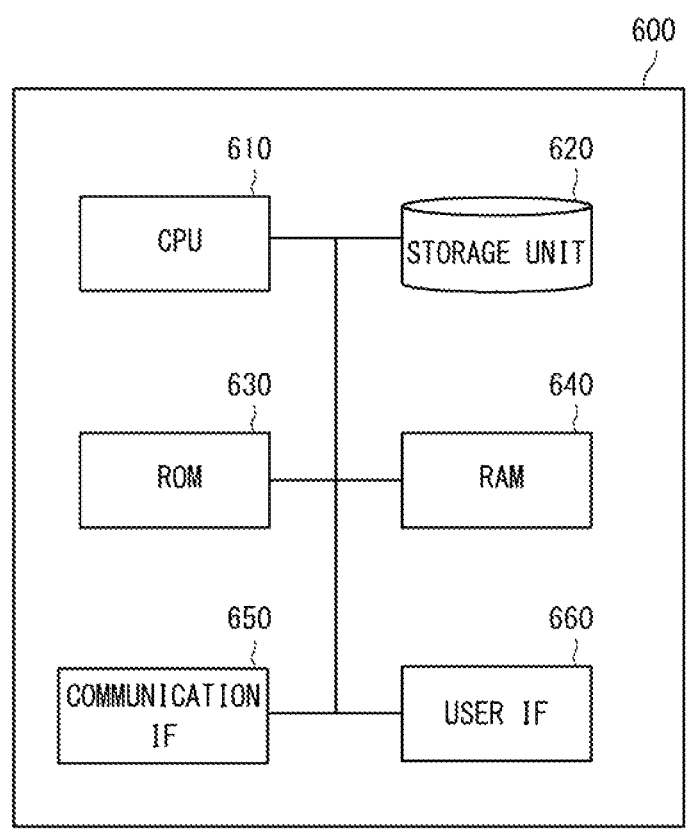
FIG. 5 is a block diagram showing an example of a configuration of a computer apparatus.

In each of above-described example embodiments, the controller 500 can be formed as a computer apparatus. FIG. 5 shows an example of a configuration of an information processing apparatus (a computer apparatus) that can be used for the controller 500. An information processing apparatus 600 includes a control unit (CPU: Central Processing Unit) 610, a storage unit 620, a ROM (Read Only Memory) 630, a RAM (Random Access Memory) 640, a communication interface (IF: Interface) 650, and a user interface 660.

The communication interface 650 is an interface for connecting the information processing apparatus 600 to a communication network through wired communication means, wireless communication means, or the like. The user interface 660 includes, for example, a display unit such as a display. Further, the user interface 660 includes an input unit such as a keyboard, a mouse, and a touch panel.

The storage unit 620 is an auxiliary storage device that can hold various types of data. The storage unit 620 does not necessarily have to be a part of the information processing unit 600, and may be an external storage device or a cloud storage connected to the information processing unit 600 through a network. The ROM 630 is a non-volatile storage device. For example, a semiconductor storage device such as a flash memory having relatively small capacity is used for the ROM 630. Programs executed by the CPU 610 can be stored in the storage unit 620 or the ROM 630.

The aforementioned program can be stored and provided to the information processing apparatus 600 by using any type of non-transitory computer readable media. Non-transitory computer readable media include any type of tangible storage media. Examples of non-transitory computer readable media include magnetic storage media such as floppy disks, magnetic tapes, and hard disk drives, optical magnetic storage media such as magneto-optical disks, optical disk media such as CD (Compact Disc) and DVD (Digital Versatile Disk), and semiconductor memories such as mask ROM, PROM (Programmable ROM), EPROM (Erasable PROM), flash ROM, and RAM. Further, the program may be provided to a computer using any type of transitory computer readable media. Examples of transitory computer readable media include electric signals, optical signals, and electromagnetic waves. Transitory computer readable media can provide the program to a computer via a wired communication line such as electric wires and optical fibers or a radio communication line.

The RAM 640 is a volatile storage device. As the RAM 640, various types of semiconductor memory apparatuses such as a DRAM (Dynamic Random Access Memory) or an SRAM (Static Random Access Memory) can be used. The RAM 640 can be used as an internal buffer for temporarily storing data and the like. The CPU 610 expands (i.e., loads) a program stored in the storage unit 620 or the ROM 630 in the RAM 640, and executes the expanded (i.e., loaded) program. By executing the program, the CPU 610 performs various types of control including, for example, guiding control, illumination control, and iris image pick-up control. Further, by the CPU 610 executing the program, various types of processing including an image processing method related to blinking are executed.

Although example embodiments according to the present disclosure have been described above in detail, the present disclosure is not limited to the above-described example embodiments, and the present disclosure also includes those that are obtained by making changes or modifications to the above-described example embodiments without departing from the spirit of the present disclosure.

For example, the whole or part of the example embodiments disclosed above can be described as, but not limited to, the following supplementary notes.

(Supplementary note 1)

An image processing system comprising:
- a plurality of iris image pick-up means disposed at mutually different positions in the same field of view;
- overall image pick-up means for performing image pick-up over a wider field of view than the field of view of the iris image pick-up means;
- guiding means for guiding a subject;
- illumination means for illuminating the subject with light; and
- control means for controlling, using an image from the overall image pick-up means, at least one of reading out an image from the plurality of iris image pick-up means, presenting at least one of an image and a sound through the guiding means, or providing illumination with light from the illumination means, wherein the control means further predicts a period in which the subject will blink next and a period in which the subject will pass through a focusing point of the iris image pick-up means, and in a case where the period in which the subject will blink next overlaps with the period in which the subject will pass through the focusing point, the control means controls at least one of the guiding means or the iris image pick-up means such that the focusing point and a position where the subject will blink next are different.

(Supplementary note 2)

The image processing system according to Supplementary note 1, wherein the control means performs readout of an image from the plurality of iris image pick-up means, and in the readout of an image from the plurality of iris image pick-up means, the control means specifies an iris image pick-up means capable of performing image pick-up of an eye of the subject from among the plurality of iris image pick-up means on the basis of an image acquired by the overall image pick-up means, sets a region of interest including the position of the eye of the subject in the specified iris image pick-up means, and acquires an image of the observation target region from the specified iris image pick-up means.

(Supplementary note 3)

The image processing system according to Supplementary note 1 or 2, wherein the control means controls the guiding means such that the subject does not blink at the focusing point in the case where the period in which the subject will blink next overlaps with the period in which the subject will pass through the focusing point.

(Supplementary note 4)

The image processing system according to Supplementary note 1 or 2, wherein the control means controls the iris image pick-up means such that the focusing point is a position other than the position of the subject in the period in which the subject will blink next in the case where the period in which the subject will blink next overlaps with the period in which the subject will pass through the focusing point.

(Supplementary note 5)

The image processing system according to Supplementary note 3 or 4, wherein the control means predicts the period in which the subject will blink next on a basis of a last time the subject blinked, a blink interval time, and a blink duration.

(Supplementary note 6)

The image processing system according to any one of Supplementary notes 3 to 5, wherein the control means predicts the period in which the subject will pass through the focusing point on a basis of a position and a movement speed of the subject.

(Supplementary note 7)

An image processing apparatus comprising:

control means for predicting a period in which a moving subject will blink next and a period in which the subject will pass through a focusing point of iris image pick-up means for performing image pick-up of an iris of the subject, and in a case where the period in which the subject will blink next overlaps with the period in which the subject will pass through the focusing point, controlling guiding means for guiding the subject such that the subject does not blink at the focusing point.

(Supplementary note 8)

The image processing apparatus according to Supplementary note 7, wherein the control means predicts the period in which the subject will blink next on a basis of a last time the subject blinked, a blink interval time, and a blink duration.

(Supplementary note 9)

The image processing apparatus according to Supplementary note 7 or 8, wherein the control means predicts the period in which the subject will pass through the focusing point on a basis of a position and a movement speed of the subject.

(Supplementary note 10)

The image processing apparatus according to any one of Supplementary notes 7 to 9, wherein the control means controls the guiding means to delay a time at which the subject will reach the focusing point in the case where the period in which the subject will blink next overlaps with the period in which the subject will pass through the focusing point.

(Supplementary note 11)

The image processing apparatus according to any one of Supplementary notes 7 to 9, wherein the control means controls the guiding means to hasten a time at which the subject will reach the focusing point in the case where the period in which the subject will blink next overlaps with the period in which the subject will pass through the focusing point.

(Supplementary note 12)

The image processing apparatus according to any one of Supplementary notes 7 to 9, wherein the control means controls the guiding means to cause the subject to blink in the case where the period in which the subject will blink next overlaps with the period in which the subject will pass through the focusing point.

(Supplementary note 13)

An image processing apparatus comprising:

control means for predicting a period in which a moving subject will blink next and a period in which the subject will pass through a focusing point of iris image pick-up means for performing image pick-up of an iris of the subject, and in a case where the period in which the subject will blink next overlaps with the period in which the subject will pass through the focusing point, controlling the iris image pick-up means such that the focusing point is a position other than the position of the subject in the period in which the subject will blink next.

(Supplementary note 14)
The image processing apparatus according to Supplementary note 13, wherein
the control means predicts the period in which the subject will blink next on a basis of a last time the subject blinked, a blink interval time, and a blink duration.

(Supplementary note 15)
The image processing apparatus according to Supplementary note 13 or 14, wherein
the control means predicts the period in which the subject will pass through the focusing point on a basis of a position and a movement speed of the subject.

(Supplementary note 16)
An image processing method comprising:
performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

(Supplementary note 17)
An image processing method comprising:
predicting a period in which a moving subject will blink next;
predicting a period in which the subject will pass through a focusing point of iris image pick-up means for performing image pick-up of an iris of the subject;
determining whether or not the period in which the subject will blink next overlaps with the period in which the subject will pass through the focusing point; and
performing, in a case of determining that the periods overlap, at least one of guiding the subject or controlling the iris image pick-up means such that the focusing point and a position where the subject will blink next are different.

(Supplementary note 18)
The image processing method according to Supplementary note 17, wherein
the subject is guided to blink next at a different position such that the subject does not blink at the focusing point in a case of determining that the period in which the subject will blink next overlaps with the period in which the subject will pass through the focusing point.

(Supplementary note 19)
The image processing method according to Supplementary note 17 or 18, wherein
the iris image pick-up means is controlled such that the focusing point is a position other than the position of the subject in the period in which the subject will blink next in a case of determining that the period in which the subject will blink next overlaps with the period in which the subject will pass through the focusing point.

(Supplementary note 20)
A non-transitory computer readable medium storing a program causing a computer to execute a process comprising:
performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

(Supplementary note 21)
A non-transitory computer readable medium storing a program causing a computer to execute a process comprising:
predicting a period in which a moving subject will blink next;
predicting a period in which the subject will pass through a focusing point of iris image pick-up means for performing image pick-up of an iris of the subject;
determining whether or not the period in which the subject will blink next overlaps with the period in which the subject will pass through the focusing point; and
performing, in a case of determining that the periods overlap, at least one of guiding the subject or controlling the iris image pick-up means such that the focusing point and a position where the subject will blink next are different.

(Supplementary note 22)
The non-transitory computer readable medium according to Supplementary note 21, wherein the program causes the computer to execute a process comprising:
guiding the subject such that the subject does not blink at the focusing point in a case of determining that the period in which the subject will blink next overlaps with the period in which the subject will pass through the focusing point.

(Supplementary note 23)
The non-transitory computer readable medium according to Supplementary note 21 or 22, wherein the program causes the computer to execute a process comprising:
controlling the iris image pick-up means such that the focusing point is a position other than the position of the subject in the period in which the subject will blink next in a case of determining that the period in which the subject will blink next overlaps with the period in which the subject will pass through the focusing point.

This application is based upon and claims the benefit of priority from Japanese patent application No. 2019-026941, filed on Feb. 18, 2019, the disclosure of which is incorporated herein in its entirety by reference.

REFERENCE SIGNS LIST

100 Overall Imaging Device
200 Guid Device
300 Illumination Device
401-404 IRIS Image Pick-Up Device
500 Controller
600 Information Processing Apparatus

What is claimed is:
1. An image processing system comprising:
a plurality of iris image pick-up cameras disposed at mutually different positions in the same field of view;
an overall image pick-up camera configured to perform image pick-up over a wider field of view than the field of view of the iris image pick-up cameras;
a speaker configured to output a sound to guide a subject;
a light source configured to illuminate the subject with light;
a processor; and
a memory storing instructions executable by the processor to:

control, using an image from the overall image pick-up camera, at least one of reading out an image from the plurality of iris image pick-up cameras, presenting the sound through the speaker, or providing illumination with the light from the light source, wherein when the subject moves toward a focusing point of the iris image pick-up camera, a period in which the subject will blink next and a period in which the subject will pass through the focusing are predicted point, and when the period in which the subject will blink next overlaps with the period in which the subject will pass through the focusing point, at least one of the speaker and or the iris image pick-up camera are controlled such that the focusing point and a position where the subject will blink next are different.

2. The image processing system according to claim 1, wherein the instructions are executable by the processor to further:

perform readout of the image from the plurality of iris image pick-up cameras; and specify, from among the plurality of iris image-pick-up cameras, an iris image pick-up camera capable of performing image pick-up of an eye of the subject based on the image acquired by the overall image pick-up camera;

set a region of interest including a position of the eye of the subject in the specified iris image pick-up camera; and acquire an image of the region of interest from the specified iris image pick-up camera.

3. The image processing system according to claim 1, wherein the speaker is controlled such that the subject does not blink at the focusing point when the period in which the subject will blink next overlaps with the period in which the subject will pass through the focusing point.

4. The image processing system according to claim 1, wherein the iris image pick-up cameras are controlled such that the focusing point is a position other than the position of the subject in the period in which the subject will blink next when the period in which the subject will blink next overlaps with the period in which the subject will pass through the focusing point.

5. The image processing system according to claim 3, wherein the period in which the subject will blink next is predicted on a basis of a last time the subject blinked, a blink interval time, and a blink duration.

6. The image processing system according to claim 3, wherein the period in which the subject will pass through the focusing point is predicted on a basis of a position and a movement speed of the subject.

7. An image processing apparatus comprising:
a processor; and
a memory storing instructions executable by the processor to:

predict, when a subject moves toward a focusing point of an iris image pick-up camera configured to perform image pick-up of an iris of the subject, a period in which the subject will blink next and a period in which the subject will pass through the focusing;

when the period in which the subject will blink next overlaps with the period in which the subject will pass through the focusing point, control a speaker to output a sound to guide the subject such that the subject does not blink at the focusing point.

8. The image processing apparatus according to claim 7, wherein the period in which the subject will blink next is predicted on a basis of a last time the subject blinked, a blink interval time, and a blink duration.

9. The image processing apparatus according to claim 7, wherein the period in which the subject will pass through the focusing point is predicted on a basis of a position and a movement speed of the subject.

10. The image processing apparatus according to claim 7, wherein the speaker is controlled to output the sound to delay a time at which the subject will reach the focusing point when the period in which the subject will blink next overlaps with the period in which the subject will pass through the focusing point.

11. The image processing apparatus according to claim 7, wherein the speaker is controlled to output the sound to hasten a time at which the subject will reach the focusing point when the period in which the subject will blink next overlaps with the period in which the subject will pass through the focusing point.

12. The image processing apparatus according to claim 7, wherein the speaker is controlled to output the sound to cause the subject to blink when the period in which the subject will blink next overlaps with the period in which the subject will pass through the focusing point.

13. An image processing method comprising:

predicting, by a processor, a period in which a subject moving toward a focusing point of an iris image pick-up camera configured to perform image pick-up of an iris of the subject will blink next;

predicting, by the processor, a period in which the subject will pass through the focusing point;

determining, by the processor, whether or not the period in which the subject will blink next overlaps with the period in which the subject will pass through the focusing point; and performing, by the processor and when the periods overlap, at least one of guiding the subject or controlling the iris image pick-up camera such that the focusing point and a position where the subject will blink next are different.

14. The image processing method according to claim 13, wherein the subject is guided such that the subject does not blink at the focusing point when the period in which the subject will blink next overlaps with the period in which the subject will pass through the focusing point.

15. The image processing method according to claim 13, wherein the iris image pick-up camera is controlled such that the focusing point is a position other than the position of the subject in the period in which the subject will blink next when the period in which the subject will blink next overlaps with the period in which the subject will pass through the focusing point.

* * * * *